United States Patent
Sheikh et al.

(10) Patent No.: US 11,320,389 B2
(45) Date of Patent: May 3, 2022

(54) LOW FREQUENCY APPARATUS AND METHOD FOR INSECT INFESTATION DETECTION

(71) Applicant: King Fahd University of Petroleum and Minerals, Dhahran (SA)

(72) Inventors: Sharif Iqbal Mitu Sheikh, Dhahran (SA); Forhad Hossain, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 455 days.

(21) Appl. No.: 16/451,888

(22) Filed: Jun. 25, 2019

(65) Prior Publication Data
US 2020/0348254 A1 Nov. 5, 2020

Related U.S. Application Data

(60) Provisional application No. 62/841,414, filed on May 1, 2019.

(51) Int. Cl.
 *G01N 27/24* (2006.01)
 *G01N 27/22* (2006.01)
 *G01N 33/00* (2006.01)

(52) U.S. Cl.
 CPC .......... *G01N 27/24* (2013.01); *G01N 27/226* (2013.01); *G01N 33/0098* (2013.01)

(58) Field of Classification Search
 None
 See application file for complete search history.

(56) References Cited

U.S. PATENT DOCUMENTS

| 2,007,879 A * | 7/1935 | Sefton | A01M 1/18 47/1.3 |
| 6,192,622 B1 | 2/2001 | Haj-Yousef | |

(Continued)

OTHER PUBLICATIONS

Sheikh ; Detection of RPW Infested Damaged Date-Palm Trees Using Dielectric Measurements ; Masters Thesis ; Aug. 2, 2018 ; Abstract Only ; 2 Pages.

*Primary Examiner* — Patrick Assouad
*Assistant Examiner* — Haidong Zhang
(74) *Attorney, Agent, or Firm* — Oblon, McClelland, Maier & Neustadt, L.L.P.

(57) ABSTRACT

An apparatus and a method for detecting insect infestation are described. The apparatus includes a cylindrical capacitive sensor including a first semi-cylindrical electrode plate and a second semi-cylindrical electrode plate, wherein the first semi and second semi-cylindrical electrode plates are configured to wrap around the test tree trunk and a processing circuitry, which is configured to measure a capacitance of the test tree trunk when positioned between the first semi-cylindrical electrode plate and the second semi-cylindrical electrode plate and provide a measured capacitance, compare the measured capacitance of the test tree trunk to a reference capacitance of a reference tree trunk, and determine whether an insect infestation is present in the test tree trunk. The cylindrical capacitive sensor can further include another two types of electrode configurations: two pairs of cylindrical electrode strips and two cylindrical electrode rings, wherein the two pairs of cylindrical electrode strips are further configured to positively charge a first pair of cylindrical electrode strips wherein the two the cylindrical electrode strips are oppositely positioned and negatively charge a second pair of cylindrical electrode strips wherein the two cylindrical electrode strips are oppositely positioned, and the two cylindrical electrode rings is further (Continued)

configured to positively charge a first cylindrical electrode ring and negatively charge a second cylindrical electrode ring.

10 Claims, 9 Drawing Sheets

(56) References Cited

U.S. PATENT DOCUMENTS

| | | |
|---|---|---|
| 6,359,597 B2 | 3/2002 | Haj-Yousef |
| 10,765,109 B1 * | 9/2020 | Dev ...................... A01M 99/00 |
| 2002/0008655 A1 * | 1/2002 | Haj-Yousef .............. G01V 3/12 |
| | | 342/22 |
| 2010/0054543 A1 | 3/2010 | Pachys |

* cited by examiner

| Diameter of tree trunk (cm) | Capacitance of healthy tree trunk (pF) | Capacitance of damaged tree trunk (pF) |
|---|---|---|
| 30 | 122 | 178 |
| 33 | 126 | 182 |
| 36 | 130 | 190 |
| 39 | 134 | 195 |
| 41 | 136 | 199 |
| 44 | 140 | 204 |
| 47 | 143 | 207 |
| 50 | 146 | 212 |

| Parameters | Sensor Configurations | | |
|---|---|---|---|
| | Two semi-cylindrical electrode plates | Two pairs of cylindrical electrode strips | Two cylindrical electrode rings |
| Capacitance in Air, $C_0$ (pF) | 13.29 | 11.93 | 12.89 |
| Capacitance for $\varepsilon_r = 80$, $C$ (pF) | 383.34 | 281.06 | 327.64 |
| Sensitivity $\frac{C - C_0}{C} \times 100\%$ | 96.5% | 95.7% | 96% |

LOW FREQUENCY APPARATUS AND METHOD FOR INSECT INFESTATION DETECTION

CROSS-REFERENCE TO RELATED APPLICATION

This present disclosure claims the benefit of U.S. Provisional Application No. 62/841,414, "Low Frequency Apparatus and method for insect infestation detection" filed on May 1, 2019, which is incorporated herein by reference in its entirety.

BACKGROUND OF THE INVENTION

Field of the Invention

The present disclosure relates to an apparatus and a method for insect infestation detection, for example Red Palm Weevil (RPW) infestation in palm trees.

Description of the Related Art

Red Palm Weevil (RPW), with a scientific name of Rhynchophorus Ferrungineus, is the most disruptive and widespread insect of palm species. Early detection of RPW infestation is critical for saving palm trees. Several approaches have been used to detect the RPW infestation in the palm trees. One approach that is widely used is based on visual inspection that observes several symptoms related to the RPW infested date palm, such as: i) presence of tunnels on the trunk, ii) presence of chewed up tissue around the opening of tunnels, iii) sugary and creamy color viscous liquid which eventually becomes brownish and oozes out from the tree trunk, iv) presence of upper dead offshoots, v) leaf stokes are worn, vi) drying of outer leaves and fruit bunches as well as breaking of the stem/crown (see V. A. Abraham, et al, "An Integrated Management Approach for Red Palm Weevil Rhynchophorus Ferrugineus Oliv. a Key Pest of Date Palm in the Middle East." *Journal of Agricultural and Marine Sciences* [S. I.], v. 3, n. 1, p. 77-83, January 1998, incorporated herein by reference in its entirety). Note that most of these symptoms only appear during the last stage of infestation and may cause the unpredicted collapse of the palm tree. A visual inspection technique is popular for detecting RPW infestation but for palm trees early infestation in the lower part of the tree trunk often remains hidden amid leaf bases or stem fibers.

Another approach commonly used is chemical detection, where a fermenting odor emitting from the wounds in an infested palm can be picked up by well-trained sniffing dogs (see V. Soroker et al., "Early Detection and Monitoring of Red Palm Weevil: Approaches and Challenges," *Association Française de Protection des Plantes (AFPP) Colloque méditerranéen sur les ravageurs des palmiers,* Nice, France, 16-18 Jan. 2013, incorporated herein by reference in its entirety). Although this technique is 70% accurate, detection comes in a later stage of RPW infestation.

In recent years, acoustic and thermal imaging techniques have become popular in detecting early stage infestation of the RPW (see N. Al-Dosary, et al, "Review on the Management of Red Palm Weevil Rhynchophorus Ferrugineus Olivier in Date Palm Phoenix Dactylifera L," *Emirates Journal of Food and Agriculture, Vol.* 28, no. 1, pp. 34-44, December 2015; V. Soroker et al., "Early Detection and Monitoring of Red Palm Weevil: Approaches and Challenges," *Association Française de Protection des Plantes (AFPP) Colloque méditerranéen sur les ravageurs des palmiers,* Nice, France, 16-18 Jan. 2013; and R. Massa et al., "Experimental and numerical evaluations on palm microwave heating for Red Palm Weevil pest control," *Nat. Publ. Gr.,* no. March, pp. 1-8, 2017, each incorporated herein by reference in their entirety). But these techniques require experienced manpower, as changes in thermal and acoustic measurements related to early stage of infestation are strongly affected by naturally occurring noise.

Infrared cameras have recently been used to detect changes in tree temperature due to RPW infestation. The main reason of temperature increase is the intensive fermentation within the tree trunk, which often exceeds 45° C. M. Mozib et al. also used this type of technique by employing a real-time temperature sensor to detect the infested palm trees (see M. Mozib and H. A. El-Shafie, "Effect of Red Palm Weevil, Rhynchophorus Ferrugineus (Olivier) Infestation on Temperature Profiles of Date Palm Tree," *J. Entomol. Nematol.,* vol. 5, no. 6, pp. 77-83, 2013, incorporated herein by reference in its entirety).

Dielectric properties are very important for the characterizing materials. There are various methods for the measurement of dielectric properties including parallel plate capacitor, coaxial probe, transmission line, resonant cavity and so on. The choice of technique can depend on many factors. Earlier work in this field estimated the approximate value of the permittivity of both healthy and infested palm trees as well as the RPW at different life stages using the coaxial probe technique (see R. Massa, et al., "Microwave Treatment for Pest Control: the Case of Rhynchophorus Ferrugineus in Phoenix Canariensis," *EPPO Bulletin,* 41: 128-135, 2011, incorporated herein by reference in its entirety). This experiment was carried out in a controlled lab environment not suitable for the field experiment because this experiment is error-prone at low frequencies and very high frequencies. Besides, it also requires expensive and sensitive equipment.

As mentioned above, the dielectric properties of healthy and infested palm trees differ significantly. Therefore, a capacitive sensing system could be a promising choice in terms of cost, stability, design flexibility as well as ease of mass use for example of large palm tree farm. The advantages of silicon fabrication technology pave the way to develop a capacitive sensing system for various applications, e.g., monitoring the phase fractions of a multi-phase fluid mixture, measuring gas/liquid volume, measuring the moisture content of soil, and measuring human blood cells (see C. T. Chiang and Y. C. Huang, "A Semi-cylindrical Capacitive Sensor with Interface Circuit Used for Flow Rate Measurement," *IEEE Sens. J.,* vol. 6, no. 6, pp. 1564-1570, 2006; A. Jaworek and A. Krupa, "Gas/Liquid Ratio Measurements by Low frequency Capacitance Sensor," *Sensors Actuators A Phys.,* vol. 113, no. 2, pp. 133-139, 2004; J. J. M. Geraets, and J. C. Borst, "A Capacitance Sensor for Two-phase Void Fraction Measurement and Flow Pattern Identification," *Int. J. Multiph. Flow,* vol. 14, 305-320, 1988; W. H. Ahmed, "Capacitance Sensors for Void-fraction Measurements and Flow-pattern Identification in Air-oil Two-phase Flow." *IEEE Sens. J.,* vol. 6, 1153-1163, 2006; M. S. A. Abouelwafa, and E. J. M. Kendall, "The Use of Capacitance Sensors for Phase Percentage Determination in Multiphase Pipelines," *IEEE Trans. Instrum. Meas.,* Vol. 29, 24-27, 1980; S. Das, T. S. Sarkar, and B. Chakraborty, "A Semi-cylindrical Capacitive Sensor Used for Soil Moisture Measurement," *Int. J. Electr. Robot. Electron. Comm. Engg.,* vol. 8, no. 1, 2014; and S. Zheng, M. S. Nandra, C. Y. Shih, W. Li, and Y. C. Tai, "Resonance Impedance Sensing of Human Blood Cells," *Sens. Actuators A: Phys.*, vol. 145-146, pp. 29-36, 2008, each incorporated herein by reference in their entirety).

Parallel plate capacitors have been used for a long time for measuring dielectric constants of planar samples. The magnitude of the capacitance depends on the electrode surface area, the distance between the electrodes and the dielectric constant of the material between the plates. However, a parallel plate arrangement is not suitable for cylindrical palm tree samples. In the present disclosure, a semi-cylindrical capacitive sensor is described that measures changes in the dielectric constant of palm trees in terms of capacitance. A numerical method is developed to measure the capacitance of healthy and damaged palm trees using this cylindrical sensor. Three different electrode configurations of this capacitor sensor have been designed and evaluated for tree capacitance measurement.

SUMMARY

Aspects of the disclosure provide an apparatus and a method for detecting insect infestation in palm trees. The apparatus can comprise a capacitive sensor including a first semi-cylindrical electrode plate and a second semi-cylindrical electrode plate, wherein the first semi and second semi-cylindrical electrode plates are configured to wrap around the test tree trunk and a processing circuitry, configured to measure a capacitance of the test tree trunk when positioned between the first semi-cylindrical electrode plate and the second semi-cylindrical electrode plate and provide a measured capacitance, compare the measured capacitance of the test tree trunk to a reference capacitance of a reference tree trunk, and determine whether an insect infestation is present in the test tree trunk.

In an embodiment, wherein the cylindrical capacitive sensor further includes another two types of electrode configurations: two pairs of cylindrical electrode strips and two cylindrical electrode rings.

In an embodiment, when the apparatus selects the two pairs of cylindrical electrode strips as the electrode configurations for the cylindrical capacitive sensor, the two pairs of cylindrical electrode strips are further configured to positively charge a first pair of cylindrical electrode strips wherein the two the cylindrical electrode strips are oppositely positioned and negatively charge a second pair of cylindrical electrode strips wherein the two cylindrical electrode strips are oppositely positioned.

In an embodiment, when the apparatus selects the two cylindrical electrode rings as the electrode configurations for the cylindrical capacitive sensor, the two cylindrical electrode rings are further configured to positively charge a first cylindrical electrode ring and negatively charge a second cylindrical electrode ring.

In an embodiment, when the cylindrical capacitive sensor includes a first semi-cylindrical electrode plate and a second semi-cylindrical electrode plate, the first semi-cylindrical electrode plate and the second semi-cylindrical electrode plate are configured to have the same height, the same radius, and a separation gap at the edges of the two semi-cylindrical electrode plates when positioned around a tree trunk.

In another embodiment, when the apparatus selects the two pairs of cylindrical electrode strips as the electrode configurations for the cylindrical capacitive sensor, the first pair of cylindrical electrode strips and the second pair of cylindrical electrode strips are configured to have the same height, the same radius, and a separation gap at the edges of each two cylindrical electrode strips when positioned around a tree trunk.

In another embodiment, when the apparatus selects the two cylindrical electrode rings as the electrode configurations for the cylindrical capacitive sensor, the first cylindrical electrode ring and the second cylindrical electrode ring are configured to have the same height, the same radius, and a separation gap at the edges of the two cylindrical electrode rings when positioned around a tree trunk.

In an embodiment, the processing circuitry is further configured to measure a capacitance of a reference test tree trunk having a known insect infestation condition and store electronically the measured capacitance of the reference test tree trunk in a storage medium of the processing circuitry.

In an embodiment, the processing circuitry of the apparatus is further configured to calculate a change between the measured capacitance of the test tree trunk and a capacitance, which is stored in a storage medium of the processing circuitry, of a healthy reference tree trunk or calculate a change between the measured capacitance of the test tree trunk and a capacitance, which is stored in a storage medium of the processing circuitry, of a damaged reference tree trunk that is caused by insect infestation.

In an embodiment, the processing circuitry of the apparatus is further configured to identify the test tree trunk to be a healthy tree trunk when a change between the measured capacitance of the test tree trunk and a capacitance of a healthy reference tree trunk does not exceed a threshold value and identify the test tree trunk to be a damaged tree trunk when the change between the measured capacitance of the test tree trunk and the capacitance of the healthy reference tree trunk exceeds the threshold value, or a change between the measured capacitance of the test tree trunk and a capacitance of a damaged reference tree trunk does not exceed a threshold value.

Aspects of the disclosure provide a method for detecting insect infestation in palm trees. The method can comprise wrapping a test tree trunk with a cylindrical capacitive sensor including a first semi-cylindrical electrode plate and a second semi-cylindrical electrode plate, positively charging the first semi-cylindrical electrode plate, negatively charging the second semi-cylindrical electrode plate, measuring, by a processing circuity, a capacitance between the first semi-cylindrical electrode plate and the second semi-cylindrical electrode plate of the test tree trunk, comparing the measured capacitance of the test tree trunk to a capacitance of a reference tree trunk, and determining whether an insect infestation is present in the test tree trunk.

Aspects of the disclosure further provide a non-transitory computer readable medium storing instructions which, when executed by a processing circuitry, cause the processing circuitry to perform a method for measuring a capacitance between the first semi-cylindrical electrode plate and the second semi-cylindrical electrode plate of the test tree trunk, comparing the measured capacitance of the test tree trunk to a capacitance of a reference tree trunk, and determining whether an insect infestation is present in the test tree trunk.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

An apparatus and a method for detecting an insect infestation are described in the present disclosure. The apparatus and the method can detect an insect infestation in an early stage without damaging the tree. Specifically, the apparatus includes a cylindrical capacitive sensor, which includes a first semi-cylindrical electrode plate and a second semi-cylindrical electrode plate, and a processing circuitry. The cylindrical capacitive sensor can be configured to mount and/or wrap around a tree trunk, positively charge the first semi-cylindrical electrode plate, and negatively charge the second semi-cylindrical electrode plate. The processing circuitry can be configured to measure a capacitance between the first semi-cylindrical electrode plate and the second semi-cylindrical electrode plate of the tree trunk, compare the measured capacitance of the tree trunk to a capacitance of a reference tree trunk, and determine whether an insect infestation is present in the tree trunk. For example, by comparing the measured capacitance of a test palm tree to a measured capacitance of a healthy reference palm tree whose insect infestation condition is known beforehand and is stored in a storage medium of the processing circuitry, the apparatus can determine whether the palm tree is damaged by the Red Palm Weevil (RPW) infestation.

Figure 1A:
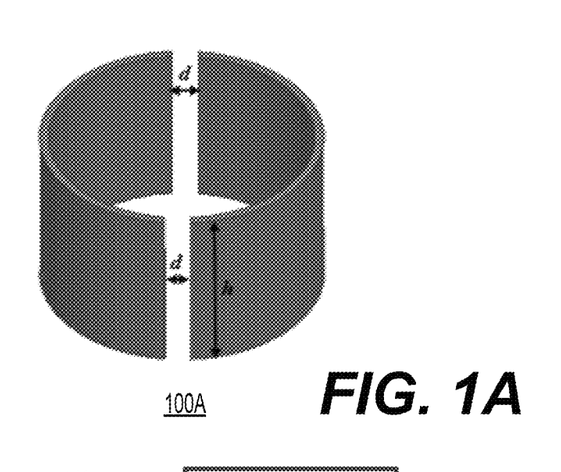
FIG. 1A is a 3-dimensional (3-D) schematic view of an exemplary cylindrical capacitive sensor according to an embodiment of the disclosure.
Figure 1B:
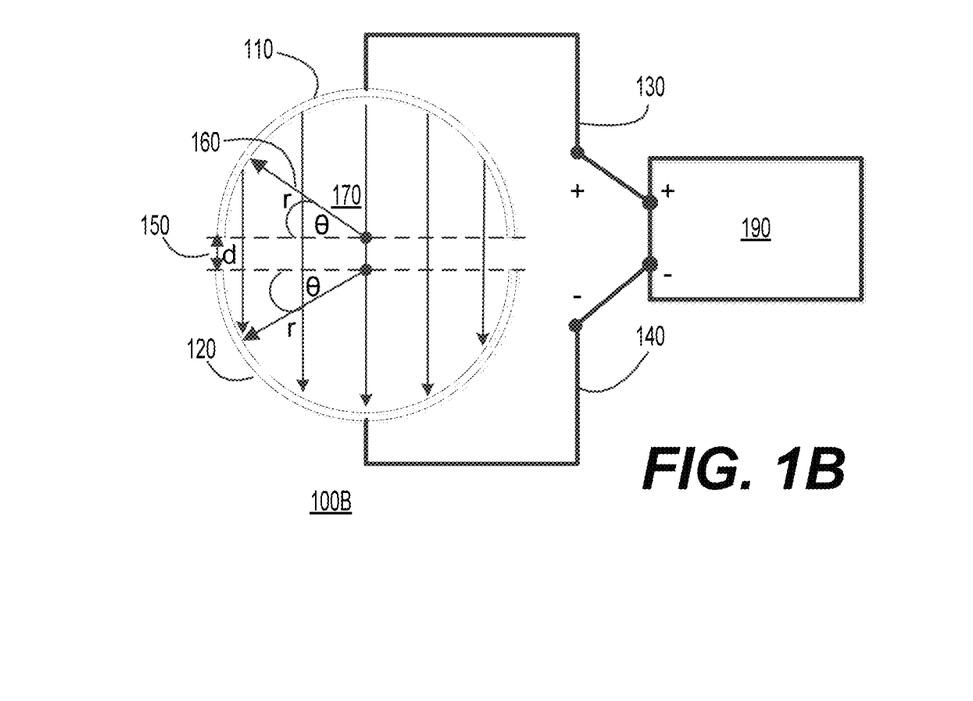
FIG. 1B is a top view of the exemplary cylindrical capacitive sensor according to an embodiment of the disclosure.
Figure 1C:
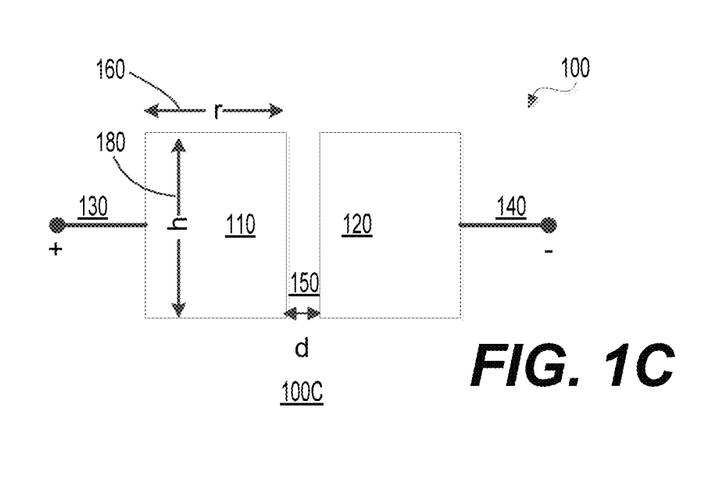
FIG. 1C is a side view of the exemplary cylindrical capacitive sensor according to an embodiment of the disclosure.

FIGS. 1A~1C shows an exemplary cylindrical capacitive sensor 100 according to an embodiment of the disclosure. The cylindrical capacitive sensor 100 can be further illustrated by a 3-dimensional (3-D) schematic view 100A, a top view 100B, and a side view 100C.

From the top view 100B and side view 100C of the FIGS. 1B-1C, the cylindrical capacitive sensor 100 can include a first semi-cylindrical electrode plate 110, a second semi-cylindrical electrode plate 120, a positive cable 130, and a negative cable 140. The first semi-cylindrical electrode plate 110 can connect to the positive cable 130 and the second semi-cylindrical electrode plate 120 can connect to the negative cable 140. In the present disclosure, the electrode plate can be any curved metallic plate. The thickness of the electrode plate can vary from 1 mm to 50 mm, preferably from 1 to 30 mm, 2 to 20 mm, 3 to 10 mm, 4 to 8 mm or about 5 mm. The height 180 of the electrode plate can vary from 1 cm to 50 cm, preferably from 5 to 30 cm, 10 to 40 cm, or about 26 cm. The radius 160 of the electrode plate is determined by the diameter of the material (e.g., tree trunk) which is placed between the first semi-cylindrical electrode plate 110 and the second semi-cylindrical electrode plate 120, and an edge gap/separation 150 between the two electrode plates. Particularly, the first semi-cylindrical electrode plate 110 and the second semi-cylindrical electrode plate 120 are very close to each other, but the material sits between them to make sure they don't touch. The edge gap/separation 150 between the two electrode plates can range from 0.1 cm~5 cm, preferably from 0.5 to 3 cm, 1 to 4 cm, or about 2 cm. In the present disclosure, the first semi-cylindrical electrode plate 110 and the second semi-cylindrical electrode plate 120 preferably have the same height 180 h=23 cm, the same thickness of 10 mm and the same radius 160 wherein the radius 160 r can vary from 15 cm to 25 cm, corresponding to the diameter of test tree trunk ranging from 30 to 50 cm. The edge gap/separation 150 is typically set to d=2 cm, but may vary.

The positive cable 130 and the negative cable 140 can be any metallic cable that connects the cylindrical capacitive sensor 100 to an electric source so that the first semi-cylindrical electrode plate 110 can be positively charged and the second semi-cylindrical electrode plate 120 can be negatively charged. Further, a measurement device, such as an oscilloscope, may be used to measure the capacitance between the first semi-cylindrical electrode plate 110 and the second semi-cylindrical electrode plate 120 in the test tree trunk. The measured capacitance of the test tree trunk can be stored in a storage medium and further compared to a reference capacitance of a reference tree trunk. In the present disclosure, a processing circuitry 190 can include the electric source, the storage medium and any other functionality that implements a process that compares the measured capacitance and determines whether an insect infestation is present in the test tree trunk. The storage medium within the processing circuitry 190 can be any device or material that can place, keep and retrieve electronic data, such as operating systems, application programs, measured capacitance, and the like. It can include a read only memory (ROM), a random access memory (RAM), a flash memory, a solid state memory, a hard disk drive, an optical disk drive, and the like.

As shown in the FIG. 1, the cavity between the first semi-cylindrical electrode plate 110 and the second semi-cylindrical electrode plate 120 is filled with an air dielectric. Although Maxwell's equations can be used to derive an exact expression, the analysis of the capacitive behavior can be difficult. By simplifying the complexity of the electrostatic analysis, a good approximation of the capacitance can be obtained. In other embodiments of the invention the cavity between the tree trunk and the electrode plates may be filled with a transmittance medium having a permittivity close top that of the tree trunk. In still other embodiments the transmittance medium may be applied to the surface of the tree trunk (smoothed or in its naturally occurring state) so that the electrode is in direct contact with the transmittance medium and/or tree trunk without any air gaps or void. The transmittance medium may be a solid moldable material, a gel, a compressible material or a liquid material that cures to form a solid support.

Comparing to a parallel plate capacitor wherein the distance between two electrode plates remains constant, the distance between the first semi-cylindrical electrode plate 110 and the second semi-cylindrical electrode plate 120 of the cylindrical capacitive sensor 100 varies along the curved surfaces with a minimum gap at the edge and a maximum gap at the center.

In order to approximate the capacitance, the first semi-cylindrical electrode plate 110 is excited with positive charge +Q and the second semi-cylindrical electrode plate 120 is with negative charge –Q. The electric field E between the two plates can be written as $$E = \frac{Q}{A\varepsilon_0}, \qquad (1)$$

wherein A=πrh is the surface area of the semi-cylindrical structure. Thus, $$E = \frac{Q}{\pi r h \varepsilon_0}. \qquad (2)$$

To calculate the electric potential difference between the plates, following equation is used $$V = \int_a^b \vec{E} \cdot d\vec{l} = \int_0^l \vec{E} \cdot d\vec{l}, \qquad (3)$$

where the edge separation/gap between the first semi-cylindrical electrode plate 110 and the second semi-cylindrical electrode plate 120 is set to d. The separation between any two points on the curved surfaces of the electrode plates 110 and 120 can be calculated by L=2r sin θ, where θ 170 is the angle between the radius 160 and horizontal plane of the curved surface. The rate of changes of the separation distance between the first semi-cylindrical electrode plate 110 and the second semi-cylindrical electrode plate 120 with respect to the angle θ 170 can be written as follows:

$$dL = 2r\cos\theta\, d\theta. \qquad (4)$$

Thus, the actual separation distance between the first semi-cylindrical electrode plate 110 and the second semi-cylindrical electrode plate 120 can be expressed as $$dl = 2r\cos\theta\, d\theta + d. \qquad (5)$$

By substituting the equation (5) into equation (3), the expression for the electric potential difference can be written as:

$$V = \frac{Qd}{\pi r h \varepsilon_0} + \int_0^\pi \frac{2Qr\cos\theta\, d\theta}{\pi r h \varepsilon_0} = \qquad (6)$$

$$\frac{Qd}{\pi r h \varepsilon_0} + \frac{2Qr\sin\theta}{\pi r h \varepsilon_0} = \frac{Q}{\pi r h \varepsilon_0}(2r\sin\theta + d)$$

for $0 \leq \theta \leq \pi$.

Thus, the capacitance between the first semi-cylindrical electrode plate 110 and the second semi-cylindrical electrode plate 120 can be expressed as $$C = \frac{Q}{V} = \frac{Q}{\frac{Q}{\pi r h \varepsilon_0}(2r\sin\theta + d)} = \frac{\pi r h \varepsilon_0}{2r\sin\theta + d}. \qquad (7)$$

In some embodiments, the two semi-cylindrical electrode plates 110 and 120 can wrap around the tree trunk, and the medium between the two plates is air and the dielectric material of the tree-trunk with either healthy or damaged tissues (due to fermentation caused by RPW). Thus, the total capacitance measurement of the semi-cylindrical capacitance sensor can be expressed as $$C_T = \sum_{n=0}^{N} \frac{\pi r h \varepsilon_0 \varepsilon_1 \varepsilon_2}{2r\sin\theta_n + d} \qquad (8)$$

where N is the number of chords, $\varepsilon_0 = 8.85 \times 10^{-12}$ and $\varepsilon_1$, $\varepsilon_2$ are a dielectric constant of air and the dielectric material of the tree trunk, respectively.

Based on the aforementioned equation, when the dielectric constant of the tree trunk changes due to the insect infestation, then the capacitance measurement also changes. Therefore, the system of the invention can differentiate between a healthy tree and an infested tree by measuring and comparing the tree capacitances.

In operation, the cylindrical capacitive sensor 100 can surround a test tree trunk. In the present disclosure, the test tree trunk can be positioned between the first semi-cylindrical electrode plate 110 and the second semi-cylindrical electrode plate 120. The first semi-cylindrical electrode plate 110 can connect to the positive cable 130 and the second semi-cylindrical electrode plate 120 can connect to the negative cable 140.

Further, the cylindrical capacitive sensor 100 can measure a capacitance of the test tree trunk. Specifically, the positive cable 130 can connect to a positive terminal of an electric source so that the first semi-cylindrical electrode plate 110 can be positively charged. Similarly, the negative cable 140 can connect to a negative terminal of the electric source so that the second semi-cylindrical electrode plate 120 can be positively charged. In some examples, the electric source can be a measurement device such as an oscilloscope which can also be used to measure the capacitance of the test tree trunk. Then the measured capacitance of the test tree trunk can be stored in the storage medium within the processing circuitry.

The cylindrical capacitive sensor 100 can then compare the measured capacitance of the test tree trunk to a capacitance of a reference tree trunk. In some examples, the capacitance of the reference tree trunk can be the capacitance of a healthy tree trunk. In some other examples, the capacitance of the reference tree trunk can be the capacitance of a damaged tree trunk which is caused by the insect infestation. The capacitance of the reference tree trunk can be measured when the insect infestation condition is known beforehand and stored electrically in the storage medium of the processing circuitry 190.

Further, the processing circuitry 190 can execute instructions that are stored in the storage medium to retrieve the measured capacitance of the test tree trunk and the capacitance of the reference tree trunk from the storage medium and compare the measured capacitance of the test tree trunk to the capacitance of the reference tree trunk. Based on the comparison result, the cylindrical capacitive sensor 100 can determine whether an insect infestation is present in the tree trunk. For example, if the reference tree trunk is a healthy tree trunk (e.g., no insect infestation), then the processing circuitry 190 can compare the measured capacitance of the test tree trunk to the capacitance of the reference healthy tree trunk. When the difference between the measured capacitance of the test tree trunk and the capacitance of the reference healthy tree trunk is below a preset threshold (e.g., 10%, 5%, 2% or 1%), then the test tree trunk can be identified to be a healthy tree trunk. Otherwise, the test tree trunk can be identified to be a damaged tree trunk.

In an alternative embodiment, if the reference tree trunk is a damaged tree trunk which is caused by insect infestation, then the processing circuitry 190 can compare the measured capacitance of the test tree trunk to the capacitance of the reference damaged tree trunk. When the difference between the measured capacitance of the test tree trunk and the capacitance of the reference damaged tree trunk is below a preset threshold (e.g., 10%, 5%, 2% or 1%), then the test tree trunk can be identified to be a damaged tree trunk.

Figure 2:
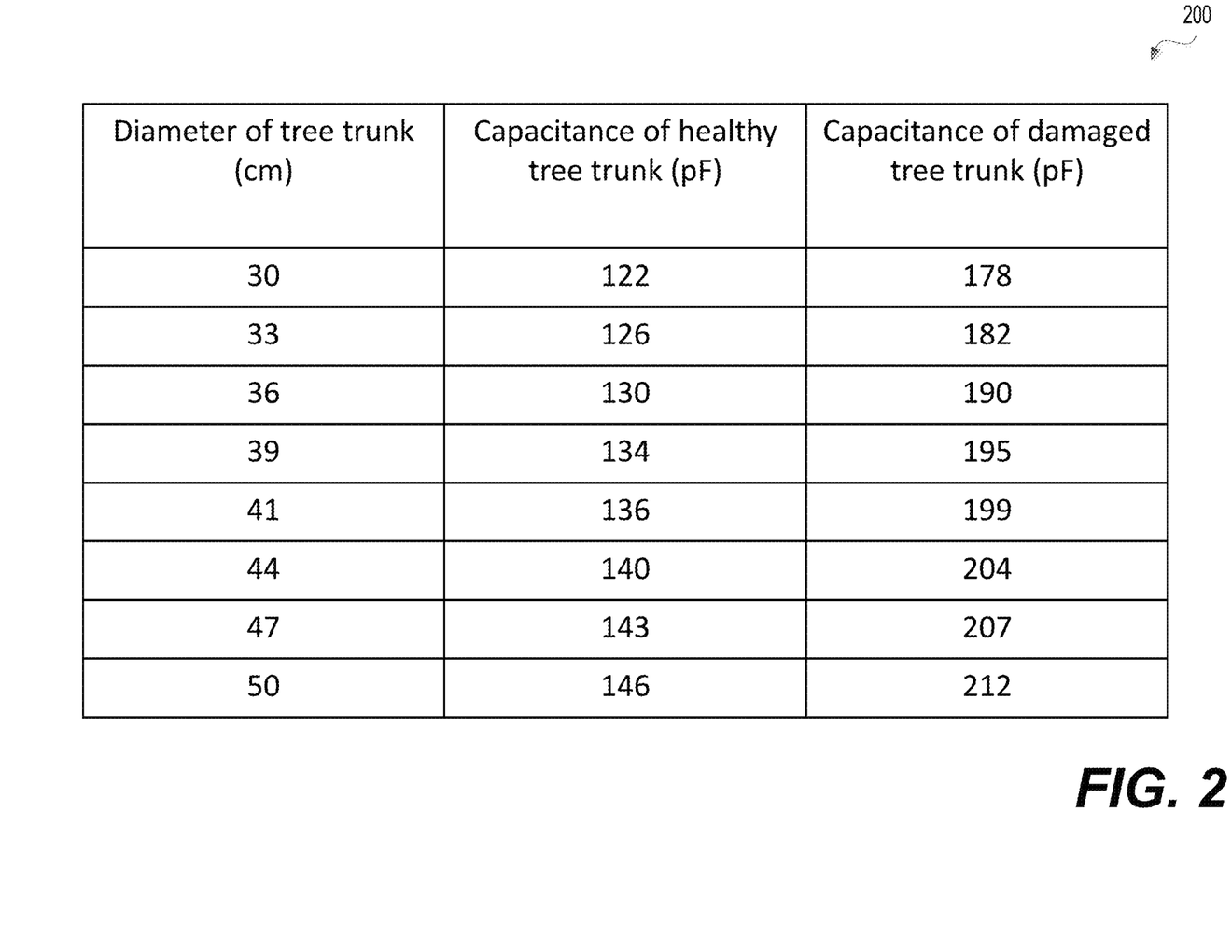
FIG. 2 is an exemplary capacitance table for a cylindrical capacitive sensor according to an embodiment of the disclosure.

FIG. 2 is a capacitance table 200 which is generated from healthy tree trunks and damaged tree trunks based on equation (8). Both the healthy and the damaged tree trunks are with different diameter values varying from 30~50 cm with an increment step size of about 3 cm. Further, the healthy and the damaged tree trunks are measured by the cylindrical capacitive sensor with a height of 23 centimeters (cm). The edge gap/separation between the first semi-cylindrical electrode plate 110 and the second semi-cylindrical electrode plate 120 that wrap each of the tree trunks is set to d=2 cm. As the diameter of the tree trunk increases from 30 cm to 50 cm, the capacitance of the healthy tree trunk increases from 122 pF to 146 pF, and the capacitance of the damaged tree trunk increases from 178 pF to 212 pF. At a specific diameter, capacitance of the damaged tree trunk is usually higher than the capacitance of the healthy tree trunk by about 55~66 pF. In addition, the difference between the capacitance of the damaged tree trunk than the capacitance of the healthy tree trunk becomes larger when the diameter of the tree trunk increases. For example, when the diameter of the tree trunk is 30 cm, the difference between the capacitance of the damaged tree trunk than the capacitance of the healthy tree trunk is 56 pF (i.e., 178 pF−122 pF=56 pF). When the diameter of the tree trunk is 50 cm, the difference goes up to 66 pF (i.e., 212 pF−146 pF=66 pF).

Damage in the tree trunk may be in the form of voids or partially filled voids. For example, the presence of an insect infestation in the tree trunk may be evident from the damage caused by the insects, e.g., voids and/or voids that are filled with degraded material. The presence of an infestation may also be evident from the presence of insects. Voids and partially filled voids inside a tree trunk produce a different dielectric constant of the tree trunk which can result to a different capacitance of the tree trunk. Therefore, the insect infestation can be are detected through comparing the capacitance of the tree trunk to a healthy tree trunk that is not infested with insects.

Figure 3:
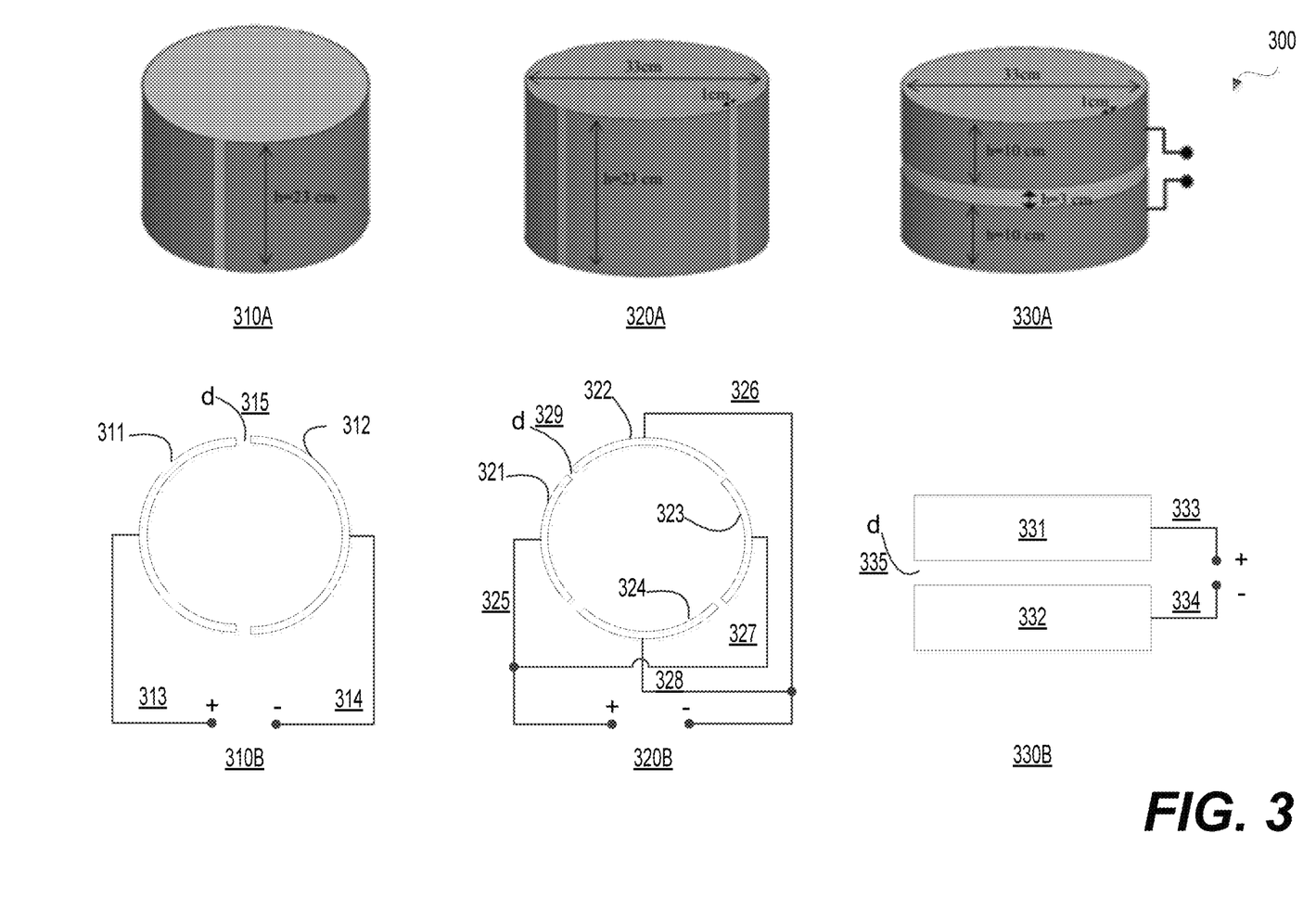
FIG. 3 shows three types of electrode configurations according to an embodiment of the disclosure.

FIG. 3 shows three types of electrode configurations 300 according to an embodiment of the disclosure. As shown in the FIG. 3, the first electrode configuration 310A and its corresponding top view 310B can include two semi-cylindrical electrode plates 311-312, second electrode configuration 320A and its corresponding top view 320B can include two pairs of cylindrical strips (e.g., four curved electrode strips) 321-324, and third electrode configuration 330A and its corresponding side view 330B can include two cylindrical electrode rings 331-332.

In the FIG. 3 example, from the top view 310B of the first electrode configuration 310A, the cylindrical capacitive sensor can include a first semi-cylindrical electrode plate 311, a second semi-cylindrical electrode plate 312, a positive cable 313, and a negative cable 314.

The semi-cylindrical electrode plate can be any curved metallic plate. The thickness of the semi-cylindrical electrode plate 311 and 312 can vary from 1 mm to 50 mm, preferably from 1 to 30 mm, 2 to 20 mm, 3 to 10 mm, 4 to 8 mm or about 5 mm. The height of the semi-cylindrical electrode plate 311 and 312 can vary from 1 cm to 50 cm, preferably from 5 to 30 cm, 10 to 40 cm, or about 26 cm. The radius of the semi-cylindrical electrode plate 311 and 312 is determined by the diameter of the material (e.g., the tree trunk) which is placed between the first semi-cylindrical electrode plate 311 and the second semi-cylindrical electrode plate 312, and an edge gap/separation 315 between the two semi-cylindrical electrode plates 311 and 312. Particularly, the first semi-cylindrical electrode plate 311 and the second semi-cylindrical electrode plate 312 are very close to each other, but the material sits between them to make sure they don't touch. The edge gap/separation 315 between the two electrode plates can range from 0.1 cm~5 cm, preferably from 0.5 to 3 cm, 1 to 4 cm, or about 2 cm. In the present disclosure, the first semi-cylindrical electrode plate 311 and the second semi-cylindrical electrode plate 312 are having the same height 23 cm, the same thickness of 10 mm and the same radius wherein the radius can vary from 15 cm to 25 cm (e.g., 17.5 cm), corresponding to the diameter of test tree trunk ranging from 30 to 50 (e.g., 33 cm). The edge gap/separation 315 is set to d=2 cm.

The positive cable 313 and the negative cable 314 can be any metallic cable that can connects the cylindrical capacitive sensor to an electric source so that the first semi-cylindrical electrode plate 311 can be positively charged and the second semi-cylindrical electrode plate 312 can be negatively charged.

From the top view 320B of the second electrode configuration 320A, the cylindrical capacitive sensor can include a first curved electrode strip 321, a second curved electrode strip 322, a third curved electrode strip 323, a fourth curved electrode strip 324, a first positive cable 325, a first negative cable 326, a second positive cable 327, and a second negative cable 328.

The curved electrode strip can be any curved metallic strip. The thickness of the curved electrode strip 321~324 can vary from 1 mm to 100 mm, preferably from 1 to 30 mm, 2 to 20 mm, 3 to 10 mm, 4 to 8 mm or about 5 mm. The height of the curved electrode strip 321~324 can vary from 1 cm to 50 cm, preferably from 5 to 30 cm, 10 to 40 cm, or about 26 cm. The radius of the curved electrode strip 321~324 is determined by the diameter of the material (e.g., the tree trunk) which is cavity formed by the curved electrode strips 321~324, and an edge gap/separation 329 between every two curved electrode strips 321~324. The edge gap/separation 329 between every two curved electrode strips 321~324 can range from 0.1 cm~5 cm, preferably from 0.5 to 3 cm, 1 to 4 cm, or about 1 cm. In the present disclosure, all the curved electrode strips 321~324 have the same height 23 cm, the same thickness of 10 mm and the same radius wherein the radius can vary from 15 cm to 25 cm (e.g., 17.5 cm), corresponding to the diameter of test tree trunk ranging from 30 to 50 (e.g., 33 cm). The edge gap/separation 315 is set to d=1 cm.

The positive cables 325 and 327 as well as the negative cables 326 and 328 can be any metallic cable wherein the first curved electrode strip 321 can connect to the first positive cable 325, the second curved electrode strip 322 can connect to the first negative cable 326, the third curved electrode strip 323 can connect to the second positive cable 327, and the fourth curved electrode strip 324 can connect to the second negative cable 328.

In the FIG. 3 example, the positive cables 325 and 327 can connect to a positive terminal of an electric source so that the first curved electrode strip 321 and the third curved electrode strip 323 can be positively charged. Similarly, the negative cables 326 and 328 can connect to a negative terminal of the electric source so that the second curved electrode strip 322 and the fourth curved electrode strip 324 can be positively charged.

From the side view 330B of the second electrode configuration 330A, the cylindrical capacitive sensor can include a first cylindrical electrode ring 331 and a second cylindrical electrode ring 332, a positive cable 333, and a negative cable 334.

The cylindrical electrode ring 331 and 332 can be any metallic ring. The thickness of the cylindrical electrode ring 331 and 332 can vary from 1 mm to 100 mm, preferably from 1 to 30 mm, 2 to 20 mm, 3 to 10 mm, 4 to 8 mm or about 5 mm. The height of the cylindrical electrode ring 331 and 332 can vary from 1 cm to 50 cm, preferably from 5 to 30 cm, 10 to 40 cm, or about 10 cm. The radius of the cylindrical electrode ring 331 and 332 is determined by the diameter of the material (e.g., the tree trunk) which is placed between the first cylindrical electrode ring 331 and the second cylindrical electrode ring 332, and a separation 335 between the two cylindrical electrode rings 331 and 332. The separation 335 between the two cylindrical electrode rings 331 and 332 can range from 0.1 cm~5 cm, preferably from 0.5 to 3 cm, 1 to 4 cm, or about 3 cm. In the present disclosure, the first cylindrical electrode ring 331 and the second cylindrical electrode ring 332 are having the same height 10 cm, the same thickness of 10 mm and the same radius wherein the radius can vary from 15 cm to 25 cm (e.g., 17.5 cm), corresponding to the diameter of test tree trunk ranging from 30 to 50 (e.g., 33 cm). The separation 335 is set to h=3 cm.

The positive cable 333 and the negative cable 334 can be any metallic cable that can connects the cylindrical capacitive sensor to an electric source so that the first cylindrical electrode ring 331 can be positively charged and the second cylindrical electrode plate 332 can be negatively charged.

Figure 4:
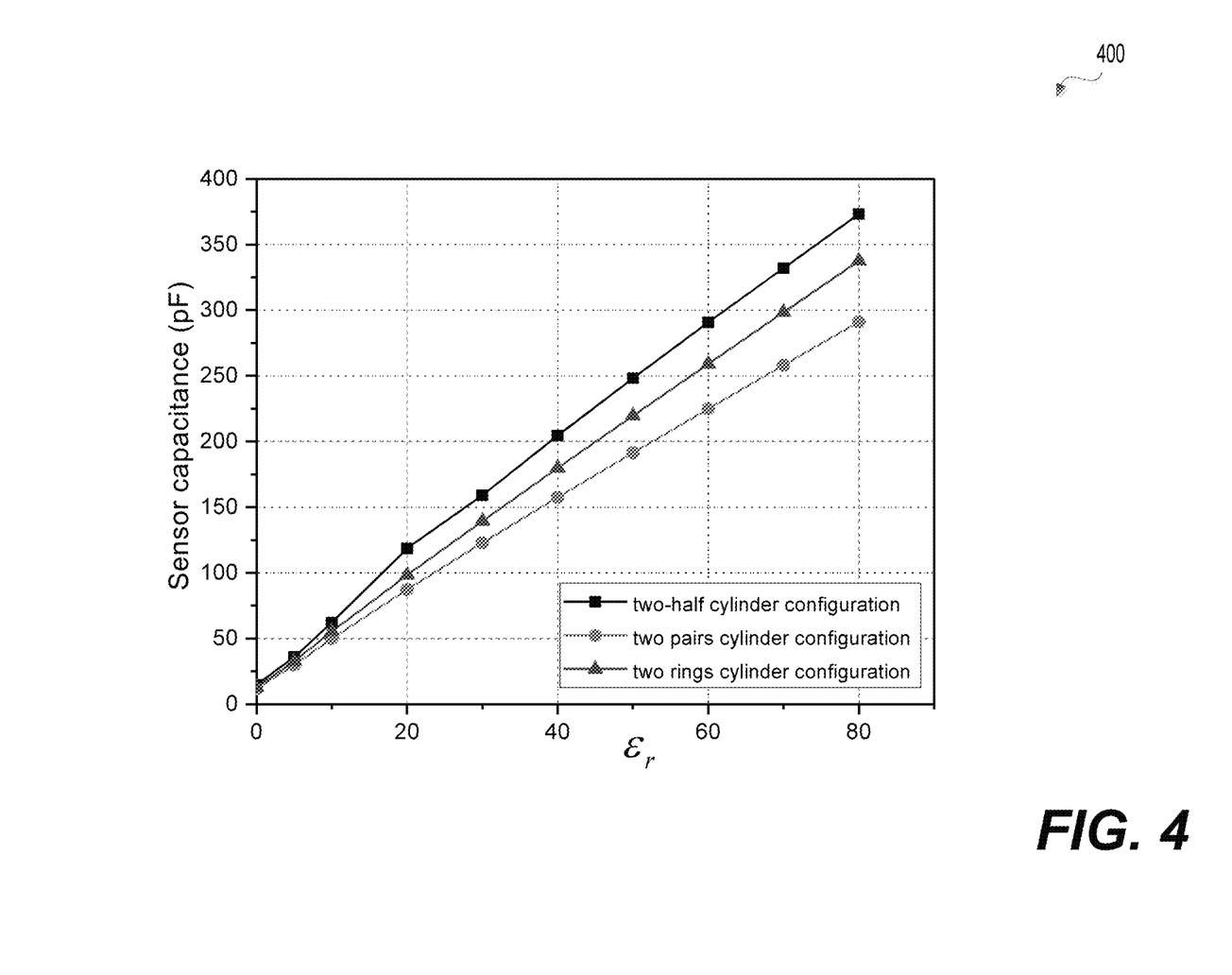
FIG. 4 is a first experimental measurement of capacitance for three types of electrodes configurations according to an embodiment of the disclosure.

FIG. 4 shows the capacitance results of three types of electrode configurations according to an embodiment of the disclosure. In the FIG. 4 example, the three electrode configurations of the cylindrical capacitive sensor are simulated by using a simulation software Ansys-Maxwell to compare the capacitance results. The simulator Ansys-Maxwell can monitor the changes in capacitance with changing dielectric properties of the material.

The cavity which is surrounded by the electrode plates is filled with air and a dielectric material, such as salty water, because the tree trunk carries water contents from soil to the leaves of the tree.

By comparing the capacitance results of these three types of electrode configurations, one of the three types of electrode configurations can be selected as the optimum design for the cylindrical capacitive sensor.

As shown in the FIG. 4, when the dielectric constant $\varepsilon_r$ increases, the sensor capacitance result increases in all of the three types of electrode configurations. Herein, $\varepsilon_r=\varepsilon_1\varepsilon_2$, $\varepsilon_1$ is the dielectric constant of air, and $\varepsilon_2$ is the dielectric constant of salty water.

Figure 5:
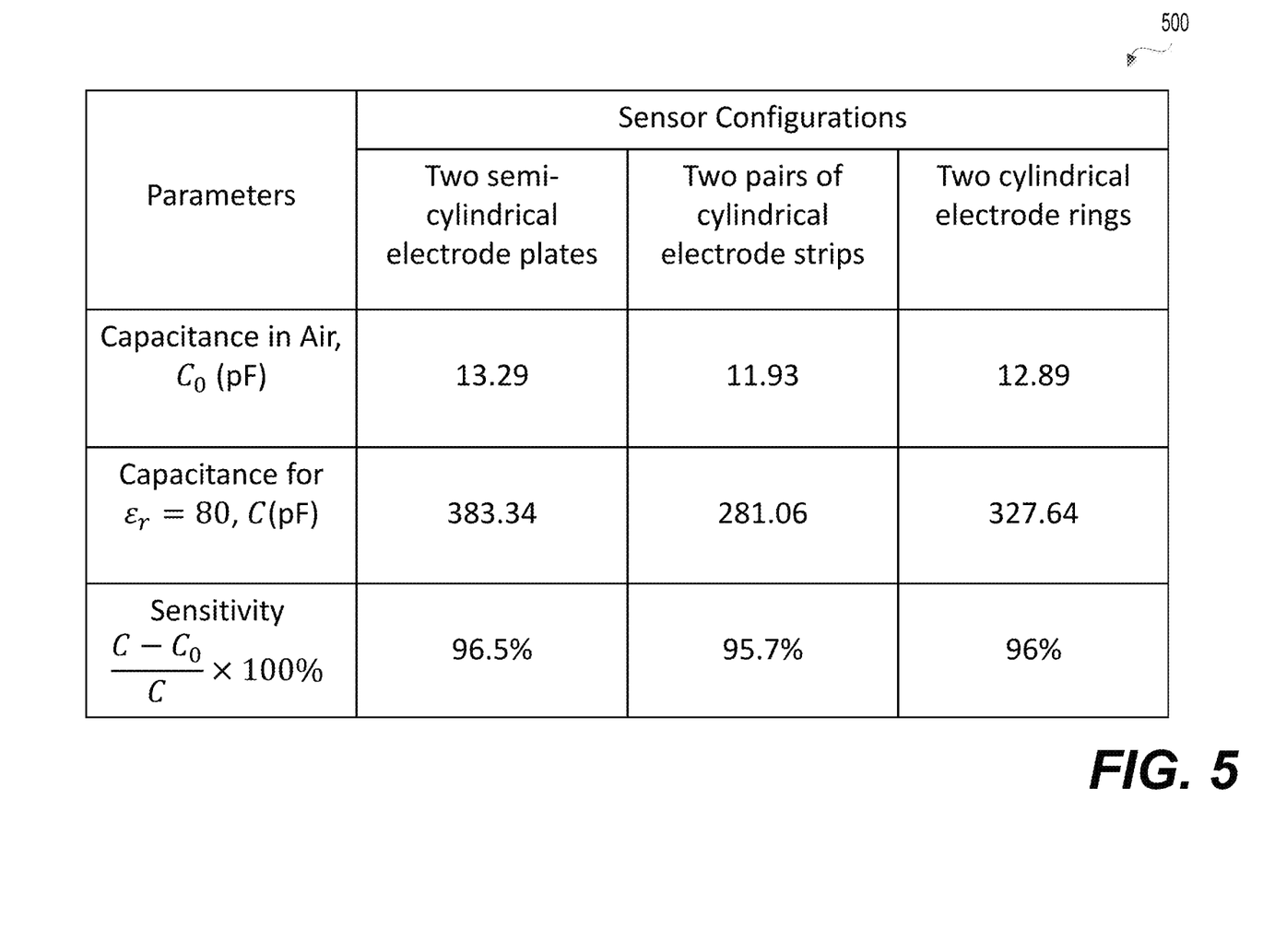
FIG. 5 is an exemplary table of capacitance sensitivities for three types of electrodes configurations according to an embodiment of the disclosure.

FIG. 5 shows a table of capacitance sensitivity for the three types of electrode configurations according to an embodiment of the disclosure. The capacitance sensitivity can be expressed as $$\frac{C-C_0}{C} \times 100\%. \tag{9}$$

By comparing the capacitance sensitivity, the cylindrical capacitive sensor can select an optimum design from one of the three types of electrode configurations.

From the FIG. 4 and FIG. 5, it can be concluded that the best-suited electrode configuration is the first electrode configuration that consists of two semi-cylindrical electrode plates (or two half-cylindrical electrode plates), because the first electrode configuration has the highest sensitivity (i.e., 96.5%) when the dielectric constant $\varepsilon_r=80$. Herein, $\varepsilon_r=\varepsilon_1\varepsilon_2$, $\varepsilon_1$ is the dielectric constant of air, and $\varepsilon_2$ is the dielectric constant of salty water.

Figure 6:
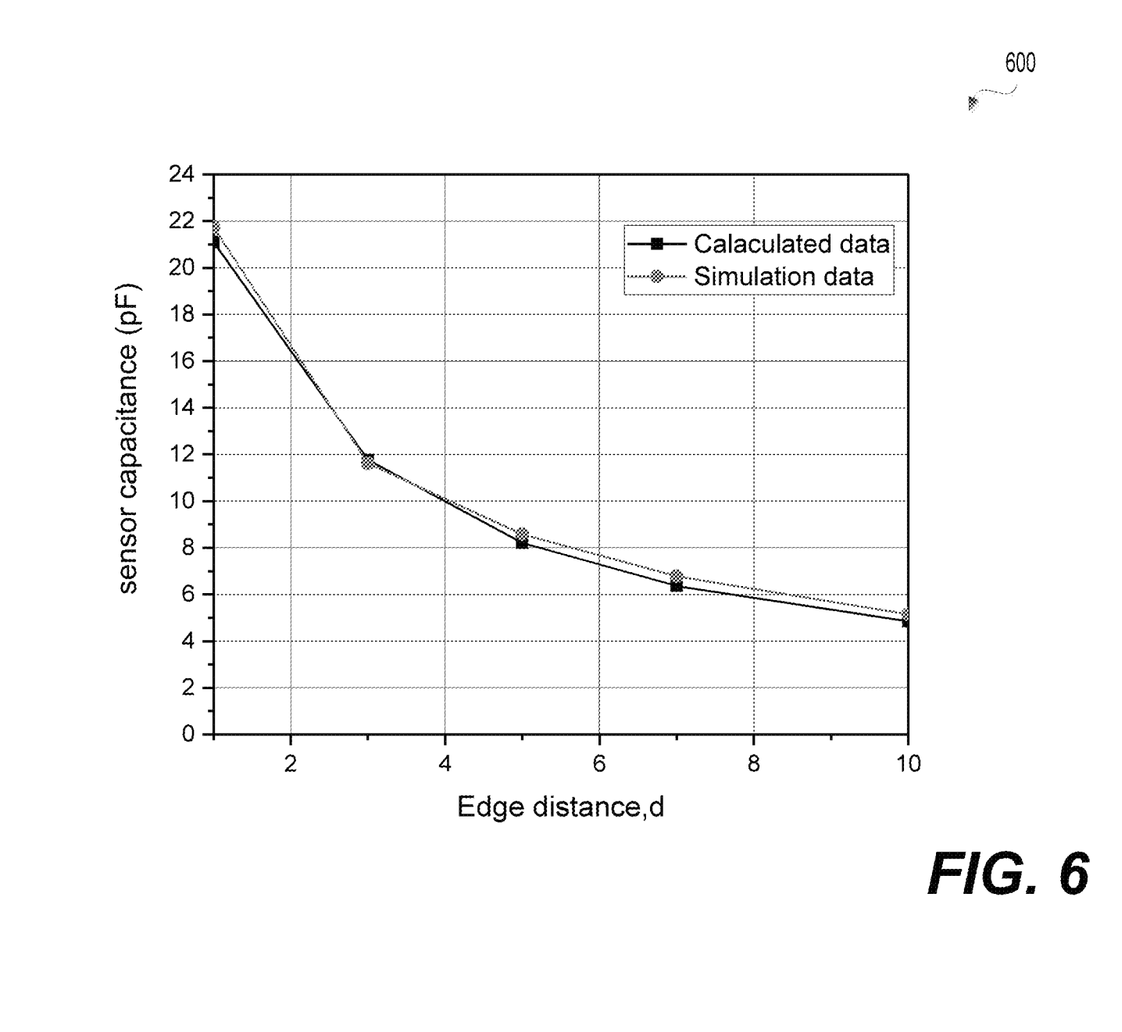
FIG. 6 is a second experimental measurement of capacitance of the semi-cylindrical air-filled electrodes with changing edge gap according to an embodiment of the disclosure.

FIG. 6 compares a calculated capacitance and a simulated capacitance with a varying edge gap according to an embodiment of the disclosure. In the FIG. 6 example, the cylindrical capacitive sensor can select the first electrode configuration that consists of two semi-cylindrical electrode plates. As the edge gap of the two semi-cylindrical electrode plates increases, the capacitance of the cylindrical capacitive sensor decreases.

Figure 7:
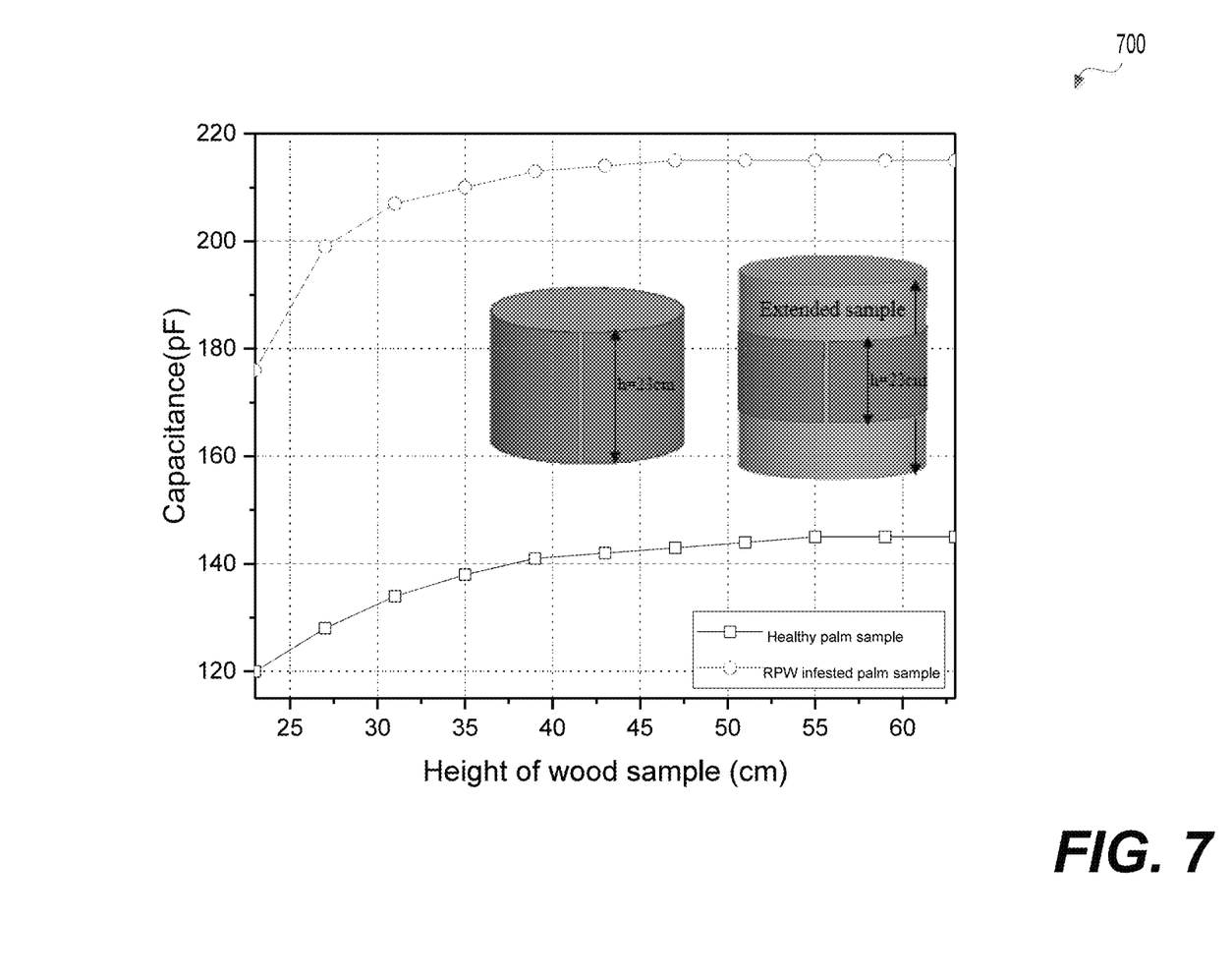
FIG. 7 is a third experimental measurement of wood capacitance variation due to extended wood sample according to an embodiment of the disclosure.

FIG. 7 shows a capacitance measurement for extended tree trunk sample according to an embodiment of the disclosure. The measurement can be performed in a cylindrical capacitive sensor that includes two semi-cylindrical electrode plates and both of the two semi-cylindrical electrode plates have the same height, e.g., h=23 cm.

In the FIG. 7 example, both a healthy tree trunk and a RPW infested tree trunk are measured and compared. The two semi-cylindrical electrode plates are configured with a diameter of 33 cm and a height of 23 cm. The gap/separation between the two semi-cylindrical electrode plates is set to 2 cm.

To make the measurement simple, instead of collecting different tree trunk samples with various stages of infestation/damage, the infestation/damage condition of the tree trunk can be controlled by injecting methanol and water mixture contents into the slightly damaged tree trunk. The designed semi-cylindrical electrode plates can be filled with the tree trunk sample. The healthy tree trunk is with uniform trunk-fiber distribution and without visible damage.

Figure 8:
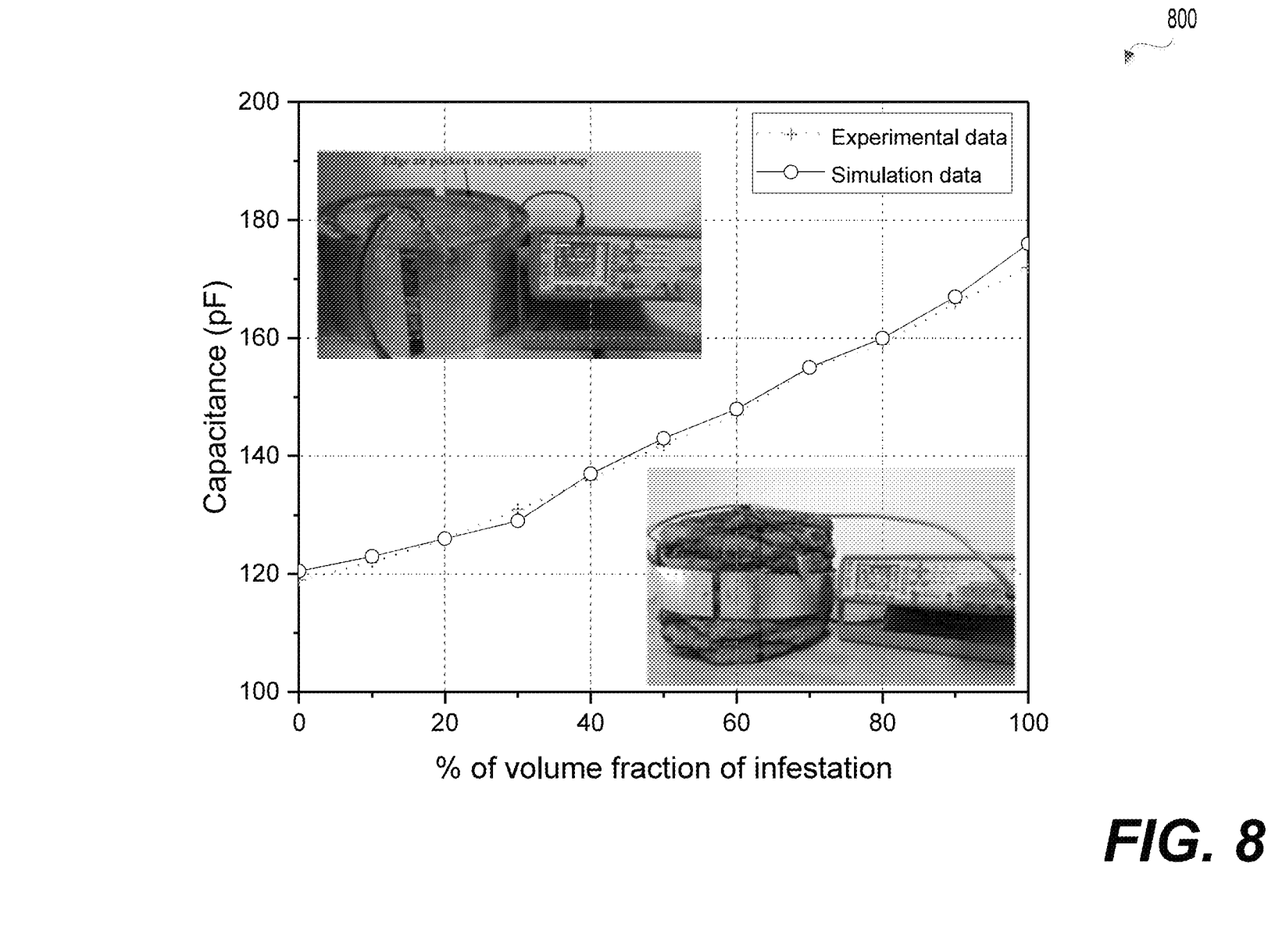
FIG. 8 is a fourth experimental measurement of capacitance variation due to the changes of the volume fraction of the damage according to an embodiment of the disclosure.

FIG. 8 shows a capacitance measurement under different tree infestation/damage conditions according to an embodiment of the disclosure. The measurement can be performed in a cylindrical capacitive sensor that includes two semi-cylindrical electrode plates and both of the two semi-cylindrical electrode plates have the same height, e.g., h=23 cm.

In the FIG. 8 example, the two semi-cylindrical electrode plates are configured with a diameter of 33 cm and a height of 23 cm. The gap/separation between the two semi-cylindrical electrode plates is set to 2 cm on both edges.

As shown in the FIG. 8, the simulated capacitance result and the experiment capacitance result coincide with each other. The simulated capacitance result and the experiment capacitance result are linear with percentage of the tree infestation/damage conditions, e.g., the percentage volume fraction of the infestation. Hence, it can be straightforward to differentiate the healthy tree and damaged tree.

Figure 9:
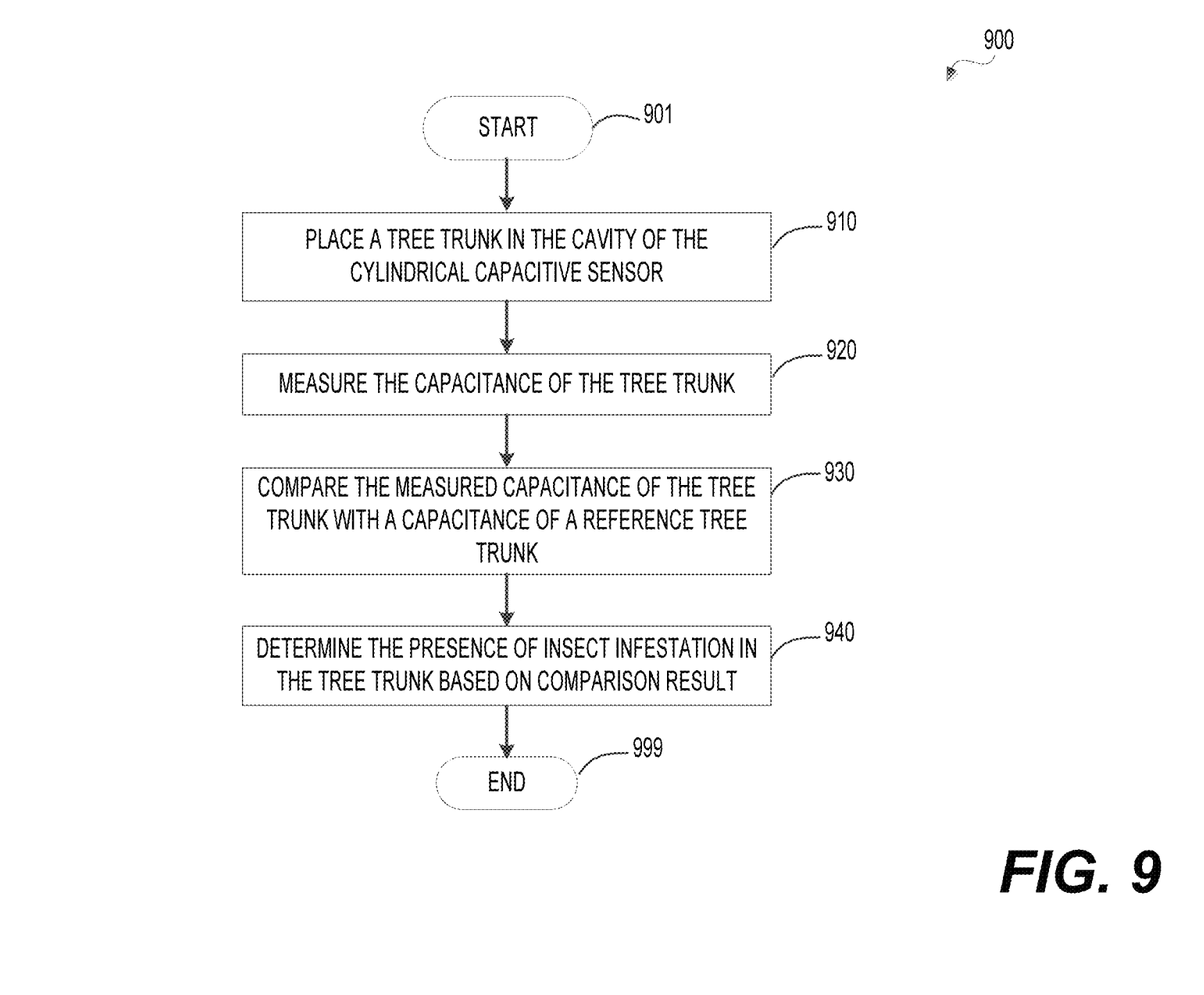
FIG. 9 is a flowchart outlining an exemplary process of detecting insect infestation according to an embodiment of the disclosure.

FIG. 9 is a flowchart outlining an exemplary process 900 of detecting insect infestation according to an embodiment of the disclosure. The process 900 can be performed at the cylindrical capacitive sensor. In the FIG. 9 example, the cylindrical capacitive sensor can select the first electrode configuration wherein a first semi-cylindrical electrode plate 311 is positively charged and a second semi-cylindrical electrode plate 312 is negatively charged, as shown in the FIG. 3. The process can start from 901 and proceed to 910.

At 910, the cylindrical capacitive sensor can surround a test tree trunk. For example, as shown in the FIG. 1, the test tree trunk 160 can be positioned between the first semi-cylindrical electrode plate 110 and the second semi-cylindrical electrode plate 120. The first semi-cylindrical electrode plate 110 can connect to the positive cable 130 and the second semi-cylindrical electrode plate 120 can connect to the negative cable 140. The process can then proceed to 920.

At 920, the capacitance of the test tree trunk between the first semi-cylindrical electrode plate 110 and the second semi-cylindrical electrode plate 120 can be measured by a measurement device, such as an oscilloscope. For example, as shown in the FIG. 1, the positive cable 130 can connect to a positive terminal of the oscilloscope so that the first semi-cylindrical electrode plate 110 can be positively charged. Similarly, the negative cable 140 can connect to a negative terminal of the oscilloscope so that the second semi-cylindrical electrode plate 120 can be negativity charged. The oscilloscope can further store the measured capacitance of the test tree trunk into the storage medium of the processing circuitry 190. The process can then proceed to 930.

At 930, the processing circuitry 190 can retrieve the measured capacitance of the test tree trunk from the storage medium and compare it to a capacitance of a reference tree trunk which is stored electronically in the storage medium of the processing circuitry 190. In some examples, the reference tree trunk can be a healthy tree trunk or a damaged tree trunk, as shown in the table 200 of the FIG. 2. The process can then proceed to 940.

At 940, the processing circuitry 190 can determine whether an insect infestation is present or not in the test tree trunk based on the comparison result. For example, if the reference tree trunk is a healthy tree trunk (e.g., no insect infestation), then the processing circuitry 190 can compare the measured capacitance of the test tree trunk to the capacitance of the reference healthy tree trunk shown in the FIG. 2. When the difference between the measured capacitance of the test tree trunk and the capacitance of the reference healthy tree trunk is below a preset threshold (e.g., 10%, 5%, 2% or 1%), then the test tree trunk can be identified to be a healthy tree trunk. Otherwise, the test tree trunk can be identified to be a damaged tree trunk. The process can then proceed to 999 and terminate.

Obviously, numerous modifications and variations of the present invention are possible in light of the above teachings. It is therefore to be understood that within the scope of the appended claims, the invention may be practiced otherwise than as specifically described herein.

The invention claimed is:

1. An apparatus for detecting insect infestation in a test tree trunk, comprising:
   a capacitive sensor including:
      a first semi-cylindrical electrode plate and a second semi-cylindrical electrode plate, wherein the first semi and second semi-cylindrical electrode plates are configured to wrap around the test tree trunk; and
      two pairs of cylindrical electrode strips configured to positively charge a first pair of cylindrical electrode strips wherein the two cylindrical electrode strips are oppositely positioned, and negatively charge a second pair of cylindrical electrode strips wherein the two cylindrical electrode strips are oppositely positioned; and a processing circuitry, configured to:
      measure a capacitance of the test tree trunk when positioned between the first semi-cylindrical electrode plate and the second semi-cylindrical electrode plate and provide a measured capacitance;
      compare the measured capacitance of the test tree trunk to a reference capacitance of a reference tree trunk; and
   determine whether an insect infestation is present in the test tree trunk.

2. The apparatus of claim 1, wherein the first semi-cylindrical electrode plate and the second semi-cylindrical electrode plate are configured to have the same height, the same radius, and a separation gap at the edges of the two semi-cylindrical electrode plates when positioned around a tree trunk.

3. The apparatus of claim 1, wherein the first pair of cylindrical electrode strips and the second pair of cylindrical electrode strips are configured to have the same height, the same radius, and a separation gap at the edges of each two cylindrical electrode strips when positioned around a tree trunk.

4. The apparatus of claim 1, wherein the processing circuitry, is further configured to:
   measure a capacitance of a reference test tree trunk having a known insect infestation condition; and
   store electronically the measured capacitance of the reference test tree trunk in a storage medium of the processing circuitry.

5. The apparatus of claim 1, wherein the processing circuitry, is further configured to:
   calculate a change between the measured capacitance of the test tree trunk and a capacitance, which is stored in a storage medium of the processing circuitry, of a healthy reference tree trunk; or
   calculate a change between the measured capacitance of the test tree trunk and a capacitance, which is stored in a storage medium of the processing circuitry, of a damaged reference tree trunk that is caused by insect infestation.

6. The apparatus of claim 1, wherein the processing circuitry, is further configured to:
   identify the test tree trunk to be a healthy tree trunk when a change between the measured capacitance of the test tree trunk and a capacitance of a healthy reference tree trunk does not exceed a threshold value; and
   identify the test tree trunk to be a damaged tree trunk when the change between the measured capacitance of the test tree trunk and the capacitance of the healthy reference tree trunk exceeds the threshold value, or a change between the measured capacitance of the test tree trunk and a capacitance of a damaged reference tree trunk does not exceed a threshold value.

7. A method for detecting insect infestation, comprising:
   wrapping a test tree trunk with a cylindrical capacitive sensor including a first semi-cylindrical electrode plate and a second semi-cylindrical electrode plate;
   positively charging the first semi-cylindrical electrode plate;
   negatively charging the second semi-cylindrical electrode plate;

measuring, by a processing circuity, a capacitance between the first semi-cylindrical electrode plate and the second semi-cylindrical electrode plate of the test tree trunk;

comparing the measured capacitance of the test tree trunk to a capacitance of a reference tree trunk; and determining whether an insect infestation is present in the test tree trunk, wherein the cylindrical capacitive sensor further includes two pairs of cylindrical electrode strips, which are configured to:

positively charge a first pair of cylindrical electrode strips wherein the two the cylindrical electrode strips are oppositely positioned; and negatively charge a second pair of cylindrical electrode strips wherein the two cylindrical electrode strips are oppositely positioned.

8. The method of claim 7, wherein the measuring, further comprises:

measuring a capacitance of a reference test tree trunk having a known insect infestation condition; and storing electronically the measured capacitance between the first semi-cylindrical electrode plate and the second semi-cylindrical electrode plate of the reference test tree trunk into a storage medium of the processing circuitry.

9. The method of claim 7, wherein the comparing, further comprises:

calculating a change between the measured capacitance of the test tree trunk and a capacitance, which is stored in a storage medium of the processing circuitry, of a healthy reference tree trunk; or calculating a change between the measured capacitance of the test tree trunk and a capacitance, which is stored in a storage medium of the processing circuitry, of a damaged reference tree trunk that is caused by insect infestation.

10. The method of claim 7, wherein the determining whether an insect infestation is present in the test tree trunk, further comprises:

identifying the test tree trunk to be a healthy tree trunk when a change between the measured capacitance of the test tree trunk and a capacitance of a healthy reference tree trunk does not exceed a threshold value; and identifying the test tree trunk to be a damaged tree trunk when the change between the measured capacitance of the test tree trunk and the capacitance of the healthy reference tree trunk exceeds the threshold value, or a change between the measured capacitance of the test tree trunk and a capacitance of a damaged reference tree trunk does not exceed a threshold value.

\* \* \* \* \*